United States Patent
Altmann

(10) Patent No.: US 10,610,179 B2
(45) Date of Patent: Apr. 7, 2020

(54) AUGMENTED REALITY GOGGLES HAVING X-RAY PROTECTION

(71) Applicant: Biosense Webster (Israel) Ltd., Yokneam (IL)

(72) Inventor: Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 229 days.

(21) Appl. No.: 15/613,496

(22) Filed: Jun. 5, 2017

(65) Prior Publication Data

US 2018/0344266 A1 Dec. 6, 2018

(51) Int. Cl.
*A61B 6/00* (2006.01)
*A61B 6/10* (2006.01)
(Continued)

(52) U.S. Cl.
CPC .............. *A61B 6/462* (2013.01); *A61B 6/107* (2013.01); *A61B 6/42* (2013.01); *A61B 6/4208* (2013.01); *A61B 6/44* (2013.01); *A61B 6/4405* (2013.01); *A61B 6/4411* (2013.01); *A61B 6/4429* (2013.01); *A61B 6/4452* (2013.01); *A61B 6/46* (2013.01); *A61B 6/461* (2013.01); *A61B 6/463* (2013.01); *A61B 6/464* (2013.01); *A61B 6/486* (2013.01); *A61B 6/487* (2013.01); *A61B 6/503* (2013.01); *A61B 6/56* (2013.01); *A61B 6/563* (2013.01); *A61B 6/566* (2013.01); (Continued)

(58) Field of Classification Search
CPC ......... A61B 6/107; A61B 6/42; A61B 6/4208; A61B 6/44; A61B 6/4405; A61B 6/4411; A61B 6/4429; A61B 6/4452; A61B 6/46; A61B 6/461; A61B 6/462; A61B 6/463; A61B 6/464; A61B 6/486; A61B 6/487; A61B 6/503; A61B 6/56; A61B 6/563; A61B 6/566
USPC ........... 378/98.5, 204, 98.8, 189; 250/370.09
See application file for complete search history.

(56) References Cited

U.S. PATENT DOCUMENTS

| 5,140,710 A | 8/1992 | Rademacher |
| 5,422,684 A | 6/1995 | Keller |

(Continued)

FOREIGN PATENT DOCUMENTS

| CN | 202060967 U | 12/2011 |
| EP | 3318214 A1 | 5/2018 |
| WO | 2018134172 A1 | 7/2018 |

OTHER PUBLICATIONS

European extended search report for corresponding European application No. EP 18175702.2, dated Oct. 4, 2018.

*Primary Examiner* — Allen C. Ho

(57) ABSTRACT

A personal display apparatus includes a dual-use transparent plate, a detector, and electronic circuitry. The dual-use transparent plate is configured to be worn by a user while the user is viewing a scene, to block, at least partially, X-rays from passing through the transparent plate and reaching an eye of the user, and to display information to be viewed by the user overlaid on the scene. The detector is coupled to the transparent plate and is configured to measure a level of the X-rays. The electronic circuitry is connected to the transparent plate and to the detector, and is configured to exchange display signals with the transparent plate so as to display the information, and to send a control signal indicative of the level of the X-rays measured by the detector.

16 Claims, 2 Drawing Sheets

(51) Int. Cl.
*H04N 5/445* (2011.01)
*G02C 7/10* (2006.01)
*G02B 27/01* (2006.01)
*G21F 1/08* (2006.01)
*G21F 1/12* (2006.01)
*A61B 34/00* (2016.01)
*A61F 9/02* (2006.01)

(52) U.S. Cl.
CPC ............ *A61B 34/25* (2016.02); *G02B 27/017* (2013.01); *G02B 27/0172* (2013.01); *G02C 7/104* (2013.01); *G21F 1/085* (2013.01); *G21F 1/125* (2013.01); *H04N 5/44504* (2013.01); *A61F 9/029* (2013.01); *G02B 2027/014* (2013.01); *G02B 2027/0141* (2013.01); *G02B 2027/0178* (2013.01)

(56) References Cited

U.S. PATENT DOCUMENTS

| | | | | |
|---|---|---|---|---|
| 5,740,222 | A | 4/1998 | Fujita et al. | |
| 6,038,467 | A * | 3/2000 | De Bliek | A61B 90/36 |
| | | | | 600/424 |
| 6,608,884 | B1 * | 8/2003 | Mazess | A61B 6/4225 |
| | | | | 378/42 |
| 6,757,416 | B2 * | 6/2004 | Kleiman | A61B 5/055 |
| | | | | 382/103 |
| 7,649,975 | B2 * | 1/2010 | Boyden | A61B 5/415 |
| | | | | 378/44 |
| 8,121,255 | B2 * | 2/2012 | Sugiyama | A61B 6/4441 |
| | | | | 378/42 |
| 8,581,932 | B2 * | 11/2013 | Kashiwagi | A61B 6/025 |
| | | | | 345/629 |
| 8,817,948 | B2 * | 8/2014 | Kusunoki | A61B 6/022 |
| | | | | 378/37 |
| 8,908,826 | B2 * | 12/2014 | Bernhardt | A61B 6/022 |
| | | | | 378/42 |
| 8,996,098 | B2 * | 3/2015 | Spector | A61B 1/00009 |
| | | | | 600/476 |
| 9,128,281 | B2 * | 9/2015 | Osterhout | G02B 27/017 |
| 9,202,301 | B2 * | 12/2015 | Sakaguchi | H04N 13/00 |
| 9,323,896 | B2 * | 4/2016 | Fält | G16B 50/00 |
| 9,341,843 | B2 * | 5/2016 | Border | G02B 27/0093 |
| 9,361,726 | B2 * | 6/2016 | Noshi | A61B 6/461 |
| 9,427,198 | B2 * | 8/2016 | Steinhauser | A61B 6/022 |
| 9,445,082 | B2 * | 9/2016 | Tsukagoshi | A61B 6/022 |
| 9,479,753 | B2 * | 10/2016 | Tsukagoshi | G02B 27/2214 |
| 9,517,041 | B2 * | 12/2016 | Melman | A61B 6/06 |
| 9,554,758 | B2 * | 1/2017 | Lim | A61B 6/107 |
| 9,615,802 | B2 * | 4/2017 | Jacobs | A61B 6/462 |
| 9,628,773 | B2 * | 4/2017 | Tsukagoshi | A61B 6/466 |
| 9,664,796 | B2 * | 5/2017 | Norrell | G01T 7/00 |
| 9,675,319 | B1 * | 6/2017 | Razzaque | A61B 8/0841 |
| 9,877,642 | B2 * | 1/2018 | Duret | A61B 6/022 |
| 9,916,691 | B2 * | 3/2018 | Takano | A61B 6/461 |
| 10,007,002 | B2 * | 6/2018 | Norrell | G01T 7/00 |
| 10,120,451 | B1 * | 11/2018 | Fram | G06F 3/017 |
| 10,143,428 | B2 * | 12/2018 | Eun | A61B 6/04 |
| 10,448,003 | B2 * | 10/2019 | Grafenberg | H04N 13/282 |
| 10,548,567 | B2 * | 2/2020 | Huepf | A61B 8/462 |
| 2015/0335298 | A1 | 11/2015 | Lim et al. | |
| 2015/0363979 | A1 | 12/2015 | Takano et al. | |

* cited by examiner

AUGMENTED REALITY GOGGLES HAVING X-RAY PROTECTION

FIELD OF THE INVENTION

The present invention relates generally to medical vision accessories, and particularly to augmented reality goggles having X-ray protection.

BACKGROUND OF THE INVENTION

Eye glasses that are protective against X-ray radiation may be used by physicians in various medical applications.

For example, U.S. Pat. No. 5,140,710, whose disclosure is incorporated herein by reference, describes an eye shield having two layers of X-radiation protective material. The shield comprises a metalized thin layer that permits the substantial transmission of accompanying visible light. Beneath the metalized thin layer is a lead layer that allows the passage of limited amounts of visible light yet functions to absorb effectively X-radiation.

Chinese utility model CN202060967U, whose disclosure is incorporated herein by reference, describes a multifunctional vision protection health care eyeshade, which comprises an eyeshade body. Two ends of the eyeshade body are connected with a lacing, and the eyeshade body is provided with an inwards concave cavity and a cover body covered on the cavity.

U.S. Pat. No. 5,422,684, whose disclosure is incorporated herein by reference, describes a form of protective eyewear having retractable eye shields which protect the wearer eyes from injury from mechanical, chemical or radiation hazards. The eye shields have an extended position and a retracted position.

SUMMARY OF THE INVENTION

An embodiment of the present invention that is described herein provides a personal display apparatus that includes a dual-use plate, a detector, and electronic circuitry. The dual-use plate is configured to be worn by a user while the user is viewing a scene, to block, at least partially, X-ray radiation from passing through the plate and reaching an eye of the user, and to display information to be viewed by the user overlaid on the scene. The detector is coupled to the plate and is configured to measure a level of the X-ray radiation. The electronic circuitry is connected to the plate and to the detector, and is configured to exchange display signals with the plate so as to display the information, and to send a control signal indicative of the level of the X-ray radiation measured by the detector.

In some embodiments, the electronic circuitry includes a transceiver, which is configured to exchange the display signals and the control signal with an external system. In other embodiments, the external system includes an imaging system. In yet other embodiments, the dual-use plate includes nanoparticles, which are configured to block the at least part of X-ray radiation.

In an embodiment, the nanoparticles include lead or cerium. In another embodiment, the dual-use plate includes at least a film of material, which is configured to block the at least part of X-ray radiation. In yet another embodiment, the electronic circuitry is configured to issue an alert in case the level of the X-ray radiation measured by the detector exceeds a predefined threshold.

In some embodiments, the scene presents an organ of a patient in which the user carries out a medical procedure. In other embodiments, the information includes at least a marker of a medical apparatus applied on the organ. In yet other embodiments, the information includes at least an anatomical image of at least part of the organ.

There is additionally provided, in accordance with an embodiment of the present invention, a method for producing a personal display apparatus, the method including providing a dual-use plate, to be worn by a user while the user is viewing a scene, the plate is capable of (i) blocking, at least partially, X-ray radiation from passing through the plate and reaching an eye of the user, and (ii) displaying information to be viewed by the user overlaid on the scene. A detector that measures a level of the X-ray radiation is coupled to the plate. Electronic circuitry is connected to the plate and to the detector, for exchanging display signals with the plate, and for sending a control signal indicative of the level of the X-ray radiation measured by the detector.

The present invention will be more fully understood from the following detailed description of the embodiments thereof, taken together with the drawings in which:

DETAILED DESCRIPTION OF EMBODIMENTS

Overview

X-ray systems, such as Fluoroscopes, are used for imaging patient organs in various medical diagnostics and surgical procedures. A physician that carries out such procedures may be exposed to excessive doses of X-ray radiation on a daily basis, and therefore may use protection measures against the radiation, such as a radiopaque apron, a toroid neck protection or an X-ray eye shield for protecting eye tissue from the radiation.

Embodiments of the present invention that are described hereinbelow provide methods and apparatus in which eye protection from the X-ray radiation, and a display used to carry out the procedure are combined.

In some embodiments, a personal display apparatus, such as goggles, is worn by the physician who may be exposed to X-ray radiation. The goggles comprise a dual-use plate, which is configured to (i) display information using augmented reality techniques, and (ii) block at least part of the X-ray radiation from passing through the plate and reaching the physician eye tissue.

In an embodiment, the goggles comprise a material that blocks at least part of the X-ray radiation. The material may be incased in the goggles, e.g., in a form of particles, or applied as a film on the goggles surface.

In some embodiments, the physician views a scene, such as an organ of a patient, while relevant information is displayed on the dual-use plate of the goggles, overlaid on the scene. The displayed information may comprise sectional images of the organ in question, markers of medical apparatus, or any other information relevant for the physician during the procedure.

In some embodiments, the goggles comprise an X-ray detector, which is configured to measure a level of the X-ray radiation in the vicinity of the goggles.

In some embodiments, the goggles comprise electronic circuitry, which is electrically connected to the plate and to the detector. The circuitry is configured to exchange display signals with the plate so as to display the information to the physician, and to send a control signal indicative of the level of the X-ray radiation measured by the detector.

The disclosed techniques enable the physician to focus his/her gaze and attention on the patient during the entire procedure, while protecting his/her eyes from the X-ray radiation and simultaneously displaying information required to carry out the procedure successfully.

System Description

Figure 1:
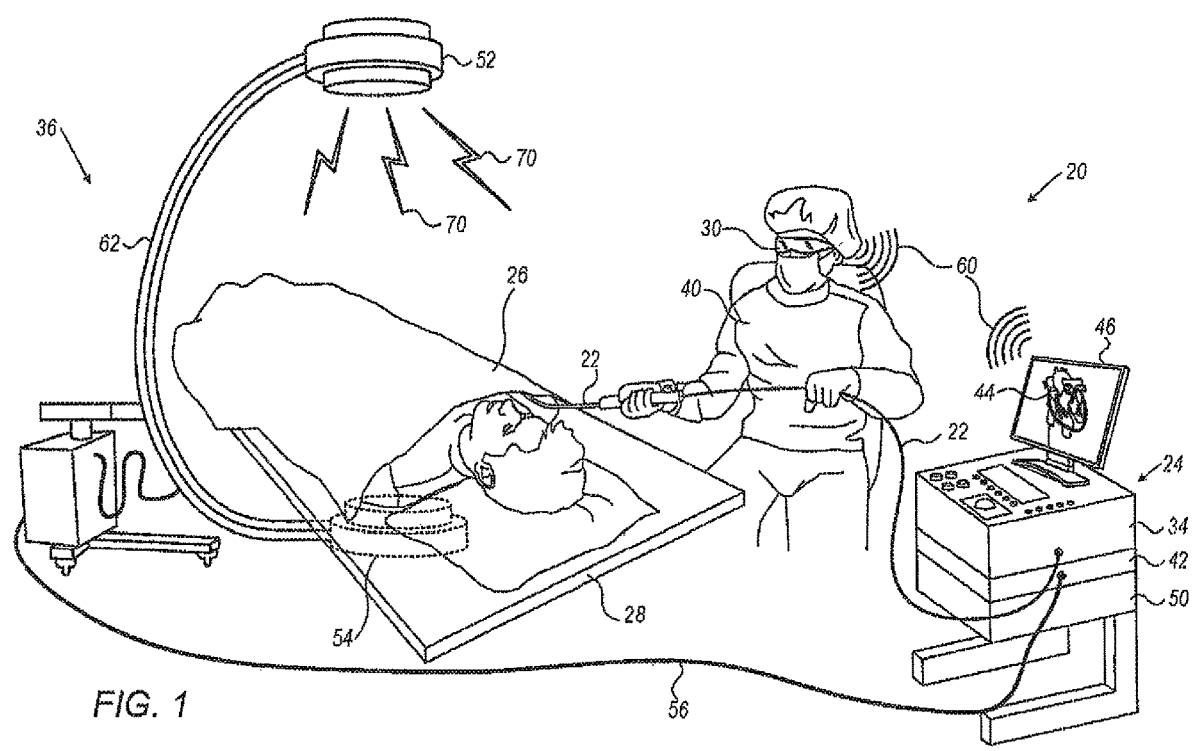
FIG. 1 is a schematic, pictorial illustration of a surgical system, in accordance with an embodiment of the present invention.

FIG. 1 is a schematic, pictorial illustration of a surgical system 20, in accordance with an embodiment of the present invention. In some embodiments, the surgical system 20 may be applied in a minimally invasive procedure, as shown in FIG. 1, in which a physician 40 carries-out the procedure using a suitable catheter 22 and an image 44 of a heart (or any other organ in question) displayed on a display 46 of a patient 26.

In other embodiments, the surgical system 20 may be applied in any other medical procedure, such as an open-heart surgery, in which physician 40 has direct visibility of the heart. In these embodiment, physician 40 may use various suitable surgical tools, instead of, or in addition to, catheter 22.

In some embodiments, the surgical system 20 comprises a fluoroscopy imaging system 36, which is configured to produce X-ray images of the organ in question (e.g., heart) of patient 26. The fluoroscopy imaging system 36 comprises an x-ray source 52 and an X-ray detector 54, which are mounted on a C-shaped arm 62. X-ray source 52 is configured to irradiate X-rays 70 on patient 26 lying on a movable table 28. The X-ray detector 54, which is located below the movable table 28, is configured to image X-rays 70 passing through patient 26.

In some embodiments, the surgical system 20 comprises a personal display, such as goggles 30, worn by physician 40. Goggles 30 are configured to partially or fully block X-rays 70 from reaching the eyes of physician 40, and to exchange display signals with an operating console 24 of the surgical system 20, so as to display information overlaid on a scene viewed by physician 40. Goggles 30 are further depicted in detail in FIGS. 2A and 2B below.

The terms "goggles" and "glasses" in the present disclosure are used interchangeably and refer to goggles 30 shown in FIG. 1, which are protective glasses used by physician 40.

In some embodiment, the operating console 24 comprises a transceiver 50, which is configured to exchange wireless signals 60 with goggles 30. In an embodiment, wireless signals 60 comprise display signals exchanged with electronic circuitry (shown in FIGS. 2A and 2B) of goggles 30. In another embodiment, wireless signals 60 may comprise communication signals that are indicative of X-ray radiation levels measured by a detector (shown in FIG. 2A) mounted on goggles 30, and transmitted from the electronic circuitry of goggles 30 to transceiver 50.

In some embodiments, the operating console 24 comprises a driver circuit 34, which drives fluoroscopy imaging system 36 via a cable 56, and is further configured to receive the X-ray radiation signals measured by the x-ray detector 54 of the fluoroscopy imaging system 36.

In some embodiments, the operating console 24 comprises a processor 42, typically a general-purpose computer, with suitable front end and interface circuits for receiving signals from multiple sources, such as the driver circuit 34, transceiver 50 and catheter 22.

In some embodiments, processor 42 is configured to produce imaging signals that are indicative of the anatomy and medical tools applied in the heart, based on the level of X-rays 70 measured by the X-ray detector 54 of the fluoroscopy imaging system 36. The medical tools may comprise catheter 22 in case of a minimally invasive procedure, and/or any suitable surgical tool used, for example, in an open-heart surgery.

Processor 42 may be programmed in software to carry out the functions that are used by the surgical system 20, and the processor stores data for the software in a memory (not shown). The software may be downloaded to the operating console 24 in electronic form, over a network, for example, or it may be provided on non-transitory tangible media, such as optical, magnetic or electronic memory media. Alternatively, some or all of the functions of processor may be carried out by dedicated or programmable digital hardware components.

Using Augmented Reality Goggles Having X-Ray Protection in a Surgical Procedure

Figure 2A:
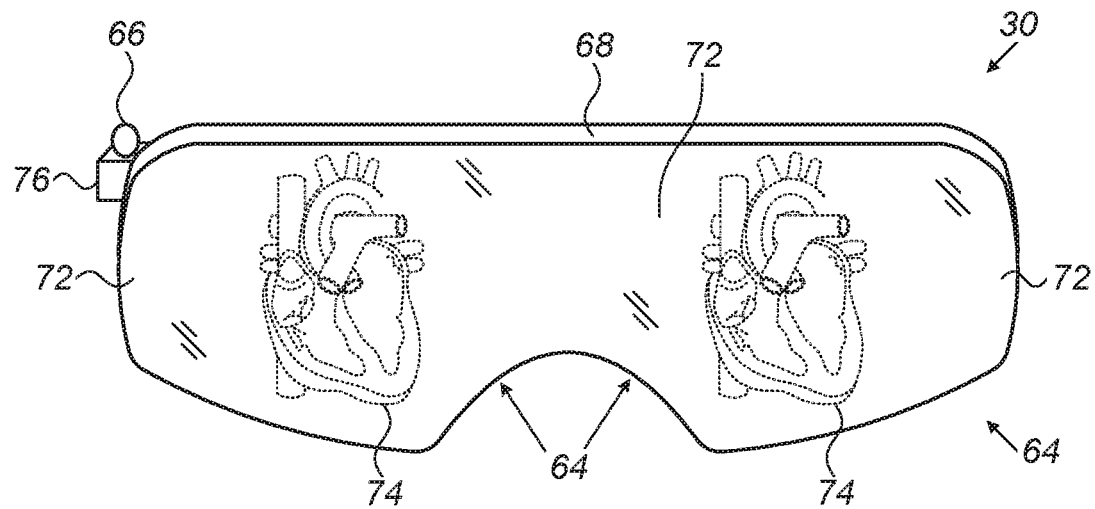
FIG. 2A is a schematic, pictorial illustration of goggles used in a medical procedure, in accordance with an embodiment of the present invention.

FIG. 2A is a schematic, pictorial illustration of goggles 30, in accordance with an embodiment of the present invention. In some embodiments, goggles 30 comprise a transparent plate 64, made from plastic or any other suitable material. The transparent plate 64 is mounted on a frame 68 made from metal of any other suitable material.

In some embodiments, goggles 30 comprise a material 72, which is applied across the entire area of the transparent plate 64, and is configured to prevent passage of at least part of the radiation of X-ray 70 from reaching into the eye tissue of physician 40.

In an embodiment, material 72 may comprise nanoparticles of cerium oxide (CeO2), and/or plumbic oxide (PbO), and/or any other suitable material distributed uniformly (or in another suitable manner) and incased in the transparent plate 64 of goggles 30.

Alternatively or additionally, material 72 may be applied as one or more films on an external surface of goggles 30, and/or as a layer embedded within the transparent plate 64.

Note that applied material 72 does not have a significant impact the transparency of the transparent plate 64.

In some embodiments, goggles 30 comprise two displays 74, one for positioning against each eye of physician 40. In other embodiments, google 30 may comprise any other suitable number of displays 74, for example, a single display positioned in front of one selected eye.

During the medical procedure, the gaze of physician 40 is directed on a distant scene, such as image 44 (in FIG. 1) in case of a minimally invasive procedure, or directly on the heart in an open-heart surgery. In some embodiments, displays 74 are configured to display information to be viewed by physician 40 overlaid on the scene.

In the example of FIG. 2A, a sectional view of a selected slice of the heart is displayed on both displays 74. In some embodiments, the selected slice is acquired by the fluoroscopy imaging system 36 and may comprise a display of catheter 22 within the heart.

In some embodiments, goggles 30 comprise a detector 66, and electronic circuitry 76, which are mounted on frame 68 or otherwise coupled to the transparent plate 64 in any other suitable manner.

In an embodiment, detector 66 is configured to measure a level of X-rays 70 impinging on goggles 30. In an embodiment, electronic circuitry 76 is mounted in close proximity to detector 66 and is configured to receive the level of the X-rays 70 measured by detector 66. The electronic circuitry 76 is depicted in detail in FIG. 2B below.

Figure 2B:
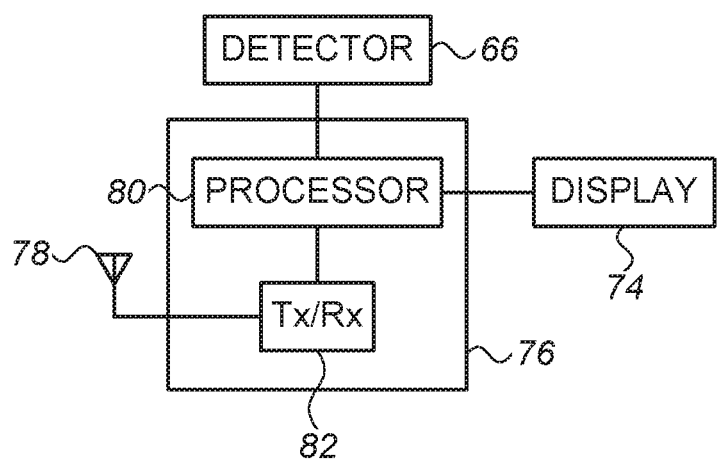
FIG. 2B is a block diagram that schematically illustrates goggles used in a medical procedure, in accordance with an embodiment of the present invention.

FIG. 2B is a block diagram that schematically illustrates the electronic circuitry 76 of goggles 30, in accordance with an embodiment of the present invention. In some embodiments, the electronic circuitry 76 comprises a processor 80 and a transceiver 82. In some embodiments, transceiver 82 connects to an antenna 78, and is configured to exchange wireless signals 60 (via antenna 78) with transceiver 50 of the operating console 24. In an embodiment, wireless signals 60 may comprise display signals exchanged between processor 42 of the operating console 24 and processor 80 of goggles 30.

For example, processor 80 is configured to receive the display signals comprising the sectional view of the heart acquired by the fluoroscopy imaging system 36, and, based on the display signals, to display the sectional view on displays 74 of goggle 30 as depicted in FIG. 2A. In this embodiment, physician 40 can see the sectional view overlaid on a selected scene, such as image 44 (in case of a minimally invasive procedure) or directly on the heart of patient 26 during an open-heart surgery.

In another embodiment, processor 80 is configured to receive measurements of X-rays 70 measured by detector 66 (e.g., level of X-rays 70) and to produce a control signal based on the X-ray measurements. In this embodiment, the control signal is transmitted, via transceivers 82 and 50, to processor 42 that may prompt physician 40 to stop the operation of fluoroscopy imaging system 36 when the measured level of X-rays 70 exceeds a predefined limit. In an alternative embodiment, processor 80 may hold a predefined threshold of the level of the X-rays 70. In this embodiment, processor 80 is configured to issue an alert (e.g., an audible alarm) to physician 40 in case the level of the X-rays 70 measured by detector 66 exceeds the predefined threshold.

In alternative embodiments, goggles 30 are connected to the operating console 24 using a communication cable (not shown) instead of or in addition to antenna 78. In these embodiments, the information and control signals are exchanged between goggles 30 and the operating console 24, e.g., through the communication cable instead of wirelessly.

Processor 80 typically comprises a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

Although the embodiments described herein mainly address cardiac procedures, the methods and systems described herein can also be used in other applications, such as in any medical procedure that applies X-ray imaging. Furthermore, the methods and systems described herein can also be used in any medical device that may be exposed to X-ray radiation when navigating a tool within the patient body during a medical treatment, such as but not limited to, orthopedic surgery, ablation procedure in the liver, or ablation of a tumor in the lung.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A personal display apparatus, comprising:
a dual-use plate, which is configured to:
be worn by a user while the user is viewing a scene;
block, at least partially, X-ray radiation from passing through the dual-use plate and reaching an eye of the user; and
display information to be viewed by the user overlaid on the scene;
a detector, which is coupled to the dual-use plate and is configured to measure a level of the X-ray radiation; and electronic circuitry, which is connected to the dual-use plate and to the detector, and is configured to exchange display signals with the dual-use plate so as to display the information, and to send a control signal indicative of the level of the X-ray radiation measured by the detector.

2. The personal display apparatus according to claim 1, wherein the electronic circuitry comprises a transceiver, which is configured to exchange the display signals and the control signal with an external system.

3. The personal display apparatus according to claim 1, wherein the dual-use plate comprises nanoparticles, which are configured to block X-ray radiation.

4. The personal display apparatus according to claim 3, wherein the nanoparticles comprise lead or cerium.

5. The personal display apparatus according to claim 1, wherein the dual-use plate comprises at least a film of material, which is configured to block X-ray radiation.

6. The personal display apparatus according to claim 1, wherein the electronic circuitry is configured to issue an alert in case the level of the X-ray radiation measured by the detector exceeds a predefined threshold.

7. A personal display apparatus, comprising:
a dual-use plate, which is configured to:
be worn by a user while the user is viewing a scene;
block, at least partially, X-ray radiation from passing through the dual-use plate and reaching an eye of the user; and
display information to be viewed by the user overlaid on the scene;
a detector, which is coupled to the dual-use plate and is configured to measure a level of the X-ray radiation; and electronic circuitry, which is connected to the dual-use plate and to the detector, and is configured to exchange display signals with the dual-use plate so as to display the information, and to send a control signal indicative of the level of the X-ray radiation measured by the detector, wherein the electronic circuitry comprises a transceiver, which is configured to exchange the display signals and the control signal with an external system,
wherein the external system comprises an imaging system.

8. A personal display apparatus, comprising:
a dual-use plate, which is configured to:
be worn by a user while the user is viewing a scene;
block, at least partially, X-ray radiation from passing through the dual-use plate and reaching an eye of the user; and
display information to be viewed by the user overlaid on the scene;
a detector, which is coupled to the dual-use plate and is configured to measure a level of the X-ray radiation; and electronic circuitry, which is connected to the dual-use plate and to the detector, and is configured to exchange display signals with the dual-use plate so as to display the information, and to send a control signal indicative of the level of the X-ray radiation measured by the detector,
wherein the scene presents an organ of a patient in which the user carries out a medical procedure.

9. The personal display apparatus according to claim 8, wherein the information comprises at least a marker of a medical apparatus applied on the organ.

10. The personal display apparatus according to claim 8, wherein the information comprises at least an anatomical image of at least part of the organ.

11. A method for producing a personal display apparatus, the method comprising: providing a dual-use plate, to be worn by a user while the user is viewing a scene, wherein the dual-use plate is capable of (i) blocking, at least partially, X-ray radiation from passing through the dual-use plate and reaching an eye of the user, and (ii) displaying information to be viewed by the user overlaid on the scene; coupling to the dual-use plate a detector that measures a level of the X-ray radiation; and connecting to the dual-use plate and to the detector, electronic circuitry for exchanging display signals with the dual-use plate, and for sending a control signal indicative of the level of the X-ray radiation measured by the detector.

12. The method according to claim 11, wherein the electronic circuitry comprises a transceiver for exchanging the display signals and the control signal with an external system.

13. The method according to claim 12, wherein the transceiver comprises a wireless transceiver.

14. The method according to claim 11, wherein the dual-use plate comprises nanoparticles for blocking X-ray radiation.

15. The method according to claim 14, wherein the nanoparticles comprise lead or cerium.

16. The method according to claim 11, wherein the dual-use plate comprises at least a film of material for blocking X-ray radiation.

* * * * *